United States Patent
Harrison et al.

(10) Patent No.: US 6,291,460 B1
(45) Date of Patent: *Sep. 18, 2001

(54) TRIAZOLO-PYRIDAZINE DERIVATIVES AS LIGANDS FOR GABA RECEPTORS

(75) Inventors: Timothy Harrison, Great Dunmow; Timothy Jason Sparey, London; Martin Richard Teall, Bishops Stortford, all of (GB)

(73) Assignee: Merck Sharp & Dohme Limited, Terlings Park (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/582,598
(22) PCT Filed: Jan. 13, 1999
(86) PCT No.: PCT/GB99/00107
 § 371 Date: Jun. 28, 2000
 § 102(e) Date: Jun. 28, 2000
(87) PCT Pub. No.: WO99/37647
 PCT Pub. Date: Jul. 29, 1999

(30) Foreign Application Priority Data

Jan. 22, 1998 (GB) .................................... 9801397

(51) Int. Cl.[7] ..................... C07D 487/04; C07D 478/04; A61K 31/50; A61K 31/41
(52) U.S. Cl. ........................ 514/248; 544/236
(58) Field of Search ............... 544/236; 514/248

(56) References Cited

U.S. PATENT DOCUMENTS

| 4,112,095 | 9/1978 | Allen, Jr. et al. | 424/250 |
|---|---|---|---|
| 4,117,130 | 9/1978 | Allen, Jr. et al. | 424/250 |
| 4,230,705 | 10/1980 | Allen, Jr. et al. | 424/250 |
| 4,260,755 | 4/1981 | Moran et al. | 544/236 |
| 4,260,756 | 4/1981 | Moran et al. | 544/236 |
| 4,654,343 | 3/1987 | Albright et al. | 514/248 |

FOREIGN PATENT DOCUMENTS

| 27 41 763 | 9/1977 | (DE) . |
|---|---|---|
| 0 085 840 | 8/1983 | (EP) . |
| 0 134 946 | 3/1985 | (EP) . |
| 1 589 237 | 5/1991 | (GB) . |
| 2345443 | * 7/2000 | (GB) . |
| WO 98/04559 | 2/1998 | (WO) . |

OTHER PUBLICATIONS

Bayley, et al., J. Psychopharmacol., 10: 206–213 (1996).
Bristow, et al., J. Pharmacol. Exp. Ther., 279: 492–501 (1996).
Dawson, et al., Psychoparmacology, 121: 109–117 (1995).
Wafford, et al., Mol. Pharmacol., 50: 670–678 (1996).

* cited by examiner

Primary Examiner—Bruck Kifle
Assistant Examiner—Rao M. Uppu
(74) Attorney, Agent, or Firm—Shu Muk Lee; David L. Rose

(57) ABSTRACT

1,2,4-triazolo[4,3-b]pyridazine derivatives, represented by

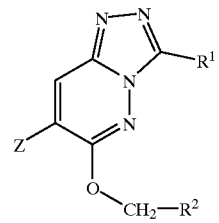

wherein Z represents cyclobutyl, 1-methylcyclopentyl or pyrrolidin-1-yl, are selective ligands for $GABA_A$ receptors, in particular having high affinity for the $\alpha 2$ and/or $\alpha 3$ subunit thereof, are useful in the treatment of anxiety and convulsions.

9 Claims, No Drawings

TRIAZOLO-PYRIDAZINE DERIVATIVES AS LIGANDS FOR GABA RECEPTORS

This is an application under 35 U.S.C. 371 of PCT/GB99/00107 and claims priority from Great Britain Application No. 9801397.2, filed Jan. 22, 1998.

The present invention relates to a class of substituted triazolo-pyridazine derivatives and to their use in therapy. More particularly, this invention is concerned with substituted 1,2,4-triazolo[4,3-b]pyridazine derivatives which are ligands for $GABA_A$ receptors and are therefore useful in the therapy of deleterious mental states.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to include at least six $\alpha$ subunits, four $\beta$ subunits, three $\gamma$ subunits, one $\delta$ subunit, one $\epsilon$ subunit and two $\rho$ subunits.

Although knowledge of the diversity of the $GABA_A$ receptor gene family represents a huge step forward in our understanding of this ligand-gated ion channel, insight into the extent of subtype diversity is still at an early stage. It has been indicated that an $\alpha$ subunit, a $\beta$ subunit and a $\gamma$ subunit constitute the minimum requirement for forming a fully functional $GABA_A$ receptor expressed by transiently transfecting cDNAs into cells. As indicated above, $\delta$, $\epsilon$ and $\rho$ subunits also exist, but are present only to a minor extent in $GABA_A$ receptor populations.

Studies of receptor size and visualisation by electron microscopy conclude that, like other members of the ligand-gated ion channel family, the native $GABA_A$ receptor exists in pentameric form. The selection of at least one $\alpha$, one $\beta$ and one $\gamma$ subunit from a repertoire of seventeen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, $\alpha 1\beta 2\gamma 2$, $\alpha 2\beta 2/3\gamma 2$, $\alpha 3\beta\gamma 2/3$, $\alpha 2\beta\gamma 1$, $\alpha 5\beta 3\gamma 2/3$, $\alpha 6\beta\gamma 2$, $\alpha 6\beta\delta$ and $\alpha 4\beta\delta$. Subtype assemblies containing an $\alpha 1$ subunit are present in most areas of the brain and are thought to account for over 40% of $GABA_A$ receptors in the rat. Subtype assemblies containing $\alpha 2$ and $\alpha 3$ subunits respectively are thought to account for about 25% and 17% of $GABA_A$ receptors in the rat. Subtype assemblies containing an $\alpha 5$ subunit are expressed predominantly in the hippocampus and cortex and are thought to represent about 4% of $GABA_A$ receptors in the rat.

A characteristic property of all known $GABA_A$ receptors is the presence of a number of modulatory sites, one of which is the benzodiazepine (BZ) binding site. The BZ binding site is the most explored of the $GABA_A$ receptor modulatory sites, and is the site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the $\alpha 1$ subunit in combination with a $\beta$ subunit and $\gamma 2$. This is the most abundant $GABA_A$ receptor subtype, and is believed to represent almost half of all $GABA_A$ receptors in the brain.

Two other major populations are the $\alpha 2\beta\gamma 2$ and $\alpha 3\beta\gamma 2/3$ subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain $\alpha 5$-containing subtype assemblies. The physiological role of these subtypes has hitherto been unclear because no sufficiently selective agonists or antagonists were known.

It is now believed that agents acting as BZ agonists at $\alpha 1\beta\gamma 2$, $\alpha 2\beta\gamma 2$ or $\alpha 3\beta\gamma 2$ subunits will possess desirable anxiolytic properties. Compounds which are modulators of the benzodiazepine binding site of the $GABA_A$ receptor by acting as BZ agonists are referred to hereinafter as "$GABA_A$ receptor agonists". The $\alpha 1$-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the $\alpha 1$ subunit. Accordingly, it is considered that $GABA_A$ receptor agonists which interact more favourably with the $\alpha 2$ and/or $\alpha 3$ subunit than with $\alpha 1$ will be effective in the treatment of anxiety with a reduced propensity to cause sedation. Also, agents which are antagonists or inverse agonists at $\alpha 1$ might be employed to reverse sedation or hypnosis caused by $\alpha 1$ agonists.

The compounds of the present invention, being selective ligands for $GABA_A$ receptors, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; depressive or bipolar disorders, for example single-episode or recurrent major depressive disorder, dysthymic disorder, bipolar I and bipolar II manic disorders, and cyclothymic disorder; psychotic disorders including schizophrenia; neurodegeneration arising from cerebral ischemia; attention deficit hyperactivity disorder; and disorders of circadian rhythm, e.g. in subjects suffering from the effects of jet lag or shift work.

Further disorders for which selective ligands for $GABA_A$ receptors may be of benefit include pain and nociception; emesis, including acute, delayed and anticipatory emesis, in particular emesis induced by chemotherapy or radiation, as well as post-operative nausea and vomiting; eating disorders including anorexia nervosa and bulimia nervosa; premenstrual syndrome; muscle spasm or spasticity, e.g. in paraplegic patients; and hearing loss. Selective ligands for $GABA_A$ receptors may also be effective as pre-medication prior to anaesthesia or minor procedures such as endoscopy, including gastric endoscopy.

In DE-A-2741763, and in U.S. Pat. Nos. 4,260,755, 4,260,756 and 4,654,343, are described various classes of 1,2,4-triazolo[4,3-b]pyridazine derivatives which are alleged to be useful as anxiolytic agents. The compounds described in DE-A-2741763 and in U.S. Pat. Nos. 4,260,755 and 4,654,343 possess a phenyl substituent at the 6-position of the triazolo-pyridazine ring system. The compounds described in U.S. Pat. No. 4,260,756, meanwhile, possess a heteroaryl moiety at the 6- or 8-position. In none of these publications, however, is there any disclosure or suggestion of 1,2,4-triazolo[4,3-b]pyridazine derivatives wherein the substituent at the 6-position is attached through a directly linked oxygen atom.

EP-A-0085840 and EP-A-0134946 describe related series of 1,2,4-triazolo[3,4-a]phthalazine derivatives which are stated to possess antianxiety activity. However, there is no disclosure nor any suggestion in either of these publications of replacing the benzo moiety of the triazolophthalazine ring system with any other functionality.

The present invention provides a class of triazolopyridazine derivatives which possess desirable binding properties at various GABA$_A$ receptor subtypes. The compounds in accordance with the present invention have good affinity as ligands for the α2 and/or α3 subunit of the human GABA$_A$ receptor. The compounds of this invention may interact more favourably with the α2 and/or α3 subunit than with the α1 subunit. Desirably, the compounds of the invention will exhibit functional selectivity in terms of a selective efficacy for the α2 and/or α3 subunit relative to the α1 subunit.

The compounds of the present invention are GABA$_A$ receptor subtype ligands having a binding affinity (K$_i$) for the α2 and/or α3 subunit, as measured in the assay described hereinbelow, of 100 nM or less, typically of 50 nM or less, and ideally of 10 nM or less. The compounds in accordance with this invention may possess at least a 2-fold, suitably at least a 5-fold, and advantageously at least a 10-fold, selective affinity for the α2 and/or α3 subunit relative to the α1 subunit. However, compounds which are not selective in terms of their binding affinity for the α2 and/or α3 subunit relative to the α1 subunit are also encompassed within the scope of the present invention; such compounds will desirably exhibit functional selectivity in terms of a selective efficacy for the α2 and/or α3 subunit relative to the α1 subunit.

The present invention provides a compound of formula I, or a pharmaceutically acceptable salt thereof:

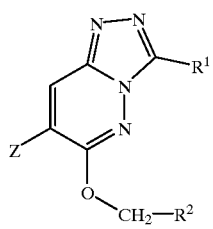

(I)

wherein
Z represents cyclobutyl, 1-methylcyclopentyl or pyrrolidin-1-yl;
R$^1$ represents pyridin-3-yl or pyridin-3-ylphenyl; and
R$^2$ represents methyl-triazolyl or methyl-pyridinyl.

The compounds in accordance with the present invention are encompassed within the generic scope of co-pending International Patent Application No. PCT/GB97/01946. There is, however, no specific disclosure therein of compounds corresponding to those of formula I as defined above.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid.

In the compounds of formula I above, the moiety Z suitably represents cyclobutyl.

Suitably, R$^1$ may represent pyridin-3-yl or 3-(pyridin-3-yl)phenyl.

The substituent R$^2$ suitably represents a ring of structure (a) or (b):

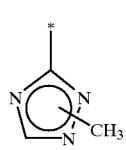

(a)

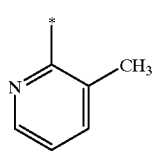

(b)

where the asterisk * denotes the point of attachment of the ring to the remainder of the molecule.

A particular moiety R$^2$ is represented by the structure (a) as depicted above. More particularly, the moiety R$^2$ may be represented by the structure (aa):

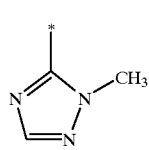

(aa)

where the asterisk * denotes the point of attachment of the ring to the remainder of the molecule.

A particular sub-class of compounds according to the invention is represented by the compounds of formula IIA, and pharmaceutically acceptable salts thereof:

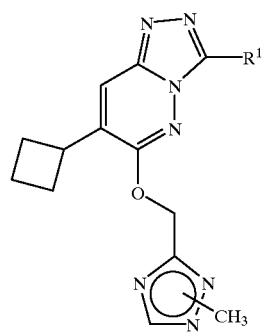

(IIA)

wherein R$^1$ is as defined above.

A particular subset of the compounds of formula IIA above is represented by the compounds of formula IIB, and pharmaceutically acceptable salts thereof:

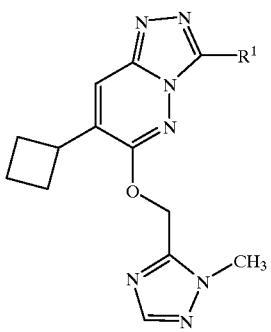

(IIB)

wherein R¹ is as defined above.

Specific compounds within the scope of the present invention include:

6-(2-methyl-2H-1,2,4-triazol-3-ylmethoxy)-3-(pyridin-3-yl)-7-(pyrrolidin-1-yl)-1,2,4-triazolo[4,3-b]pyridazine;
7-cyclobutyl-6-(2-methyl-2H-1,2,4-triazol-3-ylmethoxy)-3-(pyridin-3-yl)-1,2,4-triazolo[4,3-b]pyridazine;
7-(1-methylcyclopentyl)-6-(2-methyl-2H-1,2,4-triazol-3-ylmethoxy)-3-(pyridin-3-yl)-1,2,4-triazolo[4,3-b]pyridazine;
7-cyclobutyl-6-(2-methyl-2H-1,2,4-triazol-3-ylmethoxy)-3-[3-(pyridin-3-yl)phenyl]-1,2,4-triazolo[4,3-b]pyridazine;
6-(2-methyl-2H-1,2,4-triazol-3-ylmethoxy)-3-[3-(pyridin-3-yl)phenyl]-7-(pyrrolidin-1-yl)-1,2,4-triazolo[4,3-b]pyridazine;
7-(1-methylcyclopentyl)-6-(2-methyl-2H-1,2,4-triazol-3-ylmethoxy)-3-[3-(pyridin-3-yl)phenyl]-1,2,4-triazolo[4,3-b]pyridazine;
7-cyclobutyl-6-(3-methylpyridin-2-ylmethoxy)-3-(pyridin-3-yl)-1,2,4-triazolo[4,3-b]pyridazine;

and pharmaceutically acceptable salts thereof.

Also provided by the present invention is a method for the treatment and/or prevention of anxiety which comprises administering to a patient in need of such treatment an effective amount of a compound of formula I as defined above or a pharmaceutically acceptable salt thereof.

Further provided by the present invention is a method for the treatment and/or prevention of convulsions (e.g. in a patient suffering from epilepsy or a related disorder) which comprises administering to a patient in need of such treatment an effective amount of a compound of formula I as defined above or a pharmaceutically acceptable salt thereof.

The binding affinity ($K_i$) of the compounds according to the present invention for the α3 subunit of the human GABA$_A$ receptor is conveniently as measured in the assay described hereinbelow. The α3 subunit binding affinity ($K_i$) of the compounds of the invention is ideally 10 nM or less, preferably 2 nM or less, and more preferably 1 nM or less.

The compounds according to the present invention will ideally elicit at least a 40%, preferably at least a 50%, and more preferably at least a 60%, potentiation of the GABA $EC_{20}$ response in stably transfected recombinant cell lines expressing the α3 subunit of the human GABA$_A$ receptor. Moreover, the compounds of the invention will ideally elicit at most a 30%, preferably at most a 20%, and more preferably at most a 10%, potentiation of the GABA $EC_{20}$ response in stably transfected recombinant cell lines expressing the α1 subunit of the human GABA$_A$ receptor.

The potentiation of the GABA $EC_{20}$ response in stably transfected cell lines expressing the α3 and α1 subunits of the human GABA$_A$ receptor can conveniently be measured by procedures analogous to the protocol described in Wafford et al., *Mol. Pharmacol.*, 1996, 50, 670–678. The procedure will suitably be carried out utilising cultures of stably transfected eukaryotic cells, typically of stably transfected mouse Ltk⁻ fibroblast cells.

The compounds according to the present invention exhibit anxiolytic activity, as may be demonstrated by a positive response in the elevated plus maze and conditioned suppression of drinking tests (cf. Dawson et al., *Psychopharmacology*, 1995, 121, 109–117). Moreover, the compounds of the invention are substantially non-sedating, as may be confirmed by an appropriate result obtained from the response sensitivity (chain-pulling) test (cf. Bayley et al., *J. Psychopharmacol.*, 1996, 10, 206–213).

The compounds according to the present invention may also exhibit anticonvulsant activity. This can be demonstrated by the ability to block pentylenetetrazole-induced seizures in rats and mice, following a protocol analogous to that described by Bristow et al. in *J. Pharmacol. Exp. Ther.*, 1996, 279, 492–501.

In order to elicit their behavioural effects, the compounds of the invention will ideally be brain-penetrant; in other words, these compounds will be capable of crossing the so-called "blood-brain barrier". Preferably, the compounds of the invention will be capable of exerting their beneficial therapeutic action following administration by the oral route.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of anxiety, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds of formula I as defined above may be prepared by a process which comprises reacting a compound of formula III with a compound of formula IV:

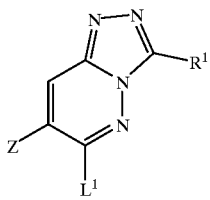

(III)

wherein Z, $R^1$ and $R^2$ are as defined above; and $L^1$ represents a suitable leaving group.

The leaving group $L^1$ is typically a halogen atom, especially chloro.

The reaction between compounds III and IV is conveniently effected by stirring the reactants in a suitable solvent, typically N,N-dimethylformamide or tetrahydrofuran, in the presence of a strong base such as sodium hydride, lithium bis(trimethylsilyl)amide or potassium bis(trimethylsilyl)amide.

The intermediates of formula III above may be prepared by reacting a compound of formula V with a substantially equimolar amount of a hydrazine derivative of formula VI:

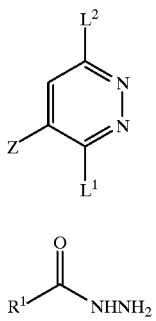

(V)

(VI)

wherein Z, $R^1$ and $L^1$ are as defined above, and $L^2$ represents a suitable leaving group; followed, if necessary, by separation of the resulting mixture of isomers by conventional means.

The leaving group $L^2$ is typically a halogen atom, especially chloro. In the intermediates of formula V, the leaving groups $L^1$ and $L^2$ may be the same or different, but are suitably the same, preferably both chloro.

The reaction between compounds V and VI is conveniently effected by heating the reactants in the presence of a proton source such as triethylamine hydrochloride, typically at reflux in an inert solvent such as xylene or 1,4-dioxane.

Alternatively, the intermediates of formula III above may be prepared by reacting a hydrazine derivative of formula VII with an aldehyde derivative of formula VIII:

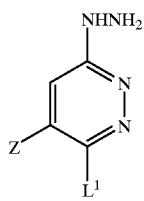

(VII)

$R^1$—CHO (VIII)

wherein Z, $R^1$ and $L^1$ are as defined above; followed by cyclization of the intermediate Schiff's base thereby obtained.

The reaction between compounds VII and VIII is conveniently effected under acidic conditions, for example in the presence of a mineral acid such as hydrochloric acid. Cyclization of the resulting Schiff's base intermediate may then conveniently be carried out by treatment with iron(III) chloride in a suitable solvent, e.g. an alcoholic solvent such as ethanol, at an elevated temperature, typically at a temperature in the region of 60–70° C.

The intermediates of formula VII above may be prepared by reacting the appropriate compound of formula V as defined above with hydrazine hydrate, typically in 1,4-dioxane at the reflux temperature of the solvent; followed, if necessary, by separation of the resulting mixture of isomers by conventional means.

In an alternative approach, the intermediates of formula III above may be prepared by reacting the hydrazine derivative of formula VII as defined above with a compound of formula IX:

$R^1$—Q (IX)

wherein $R^1$ is as defined above, and Q represents a reactive carboxylate moiety; followed by cyclization of the hydrazide derivative of formula X thereby obtained:

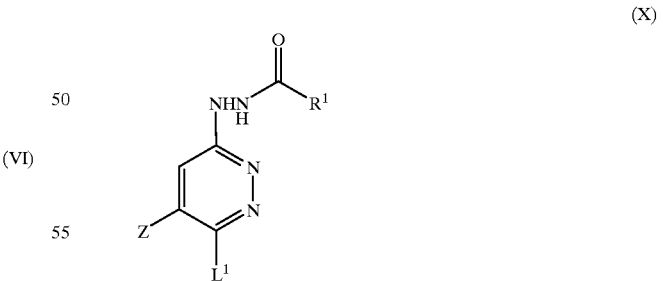

(X)

wherein Z, $R^1$ and $L^1$ are as defined above.

Suitable values for the reactive carboxylate moiety Q include esters, for example $C_{1-4}$ alkyl esters; acid anhydrides, for example mixed anhydrides with $C_{1-4}$ alkanoic acids; acid halides, for Example acid chlorides; and acylimidazoles. Suitably, Q represents an acid chloride moiety.

The reaction between compounds VII and IX is conveniently effected under basic conditions, e.g. in the presence of triethylamine, suitably in an inert solvent such as diethyl ether, and typically at a temperature in the region of 0° C. Cyclization of the resulting compound of formula X may then conveniently be carried out by treatment with 1,2-dibromo-1,1,2,2-tetrachloroethane and triphenylphosphine, in the presence of a base such as triethylamine, suitably in an inert solvent such as acetonitrile, and typically at a temperature in the region of 0° C.

The reaction between compound V and hydrazine hydrate or compound VI will, as indicated above, usually give rise to a mixture of isomeric products depending upon whether the hydrazine nitrogen atom displaces the leaving group $L^1$ or $L^2$. Thus, in addition to the required product of formula III or VII, the alternative isomer will usually be obtained to some extent. For this reason it will generally be necessary to separate the resulting mixture of isomers by conventional methods such as chromatography.

In another procedure, the compounds of formula I as defined above may be prepared by a process which comprises reacting a compound of formula XI with a compound of formula XII:

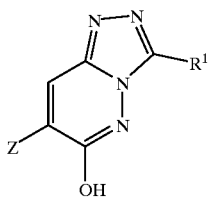

(XI)

(XII)

wherein Z, $R^1$ and $R^2$ are as defined above, and $L^3$ represents a suitable leaving group.

The leaving group $L^3$ is suitably a halogen atom, typically chloro or bromo.

The reaction between compounds XI and XII is conveniently effected by stirring the reactants in a suitable solvent, typically N,N-dimethylformamide, in the presence of a strong base such as sodium hydride.

The intermediates of formula XI above may conveniently be prepared by reacting a compound of formula III as defined above with an alkali metal hydroxide, e.g. sodium hydroxide. The reaction is conveniently effected in an inert solvent such as aqueous 1,4-dioxane, ideally at the reflux temperature of the solvent.

In a further procedure, the compounds of formula I wherein Z represents cyclobutyl or 1-methylcyclopentyl may be prepared by a process which comprises reacting a compound of formula Z—$CO_2$H with a compound of formula XIII:

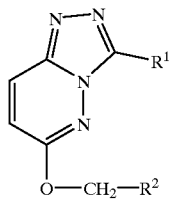

(XIII)

wherein Z, $R^1$ and $R^2$ are as defined above; in the presence of silver nitrate and ammonium persulphate.

The reaction is conveniently carried out under acidic conditions in a suitable solvent, for example using sulphuric acid in water or aqueous acetonitrile, typically at an elevated temperature.

The intermediates of formula XIII correspond to the compounds of formula I as defined above wherein Z is hydrogen, and they may therefore be prepared by methods analogous to those described above for preparing the corresponding compounds of formula I.

In a still further procedure, the compounds of formula I as defined above may be prepared by a process which comprises reacting a compound of formula XIV with a compound of formula XV:

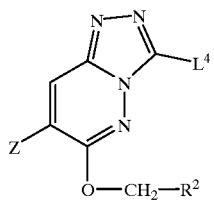

(XIV)

(XV)

wherein Z, $R^1$ and $R^2$ are as defined above, M represents —$B(OH)_2$ or —$Sn(Alk)_3$ in which Alk represents a $C_{1-6}$ alkyl group, typically n-butyl, and $L^4$ represents a suitable leaving group; in the presence of a transition metal catalyst.

The leaving group $L^4$ is suitably a halogen atom, e.g. bromo.

A suitable transition metal catalyst of use in the reaction between compounds XIV and XV comprises dichlorobis(triphenylphosphine)palladium(II) or tetrakis(triphenylphosphine)palladium(0).

The reaction between compounds XIV and XV is conveniently effected in an inert solvent such as N,N-dimethylformamide, typically at an elevated temperature.

The intermediates of formula XIV may be prepared by reacting a compound of formula IV as defined above with a compound of formula XVI:

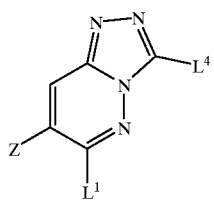

(XVI)

wherein Z, $L^1$ and $L^4$ are as defined above; under conditions analogous to those described above for the reaction between compounds III and IV.

The intermediates of formula IV above may be prepared by the procedures described in EP-A-0421210, or by methods analogous thereto.

Where they are not commercially available, the starting materials of formula V, VI, VIII, IX, XII, XV and XVI may be prepared by methods analogous to those described in the accompanying Examples, or by standard methods well known from the art.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic*

*Synthesis*, John Wiley & Sons, 1991. The protecting groups may be removed at a convenient subsequent stage using methods known from the art.

The following Examples illustrate the preparation of compounds according to the invention.

The compounds in accordance with this invention potently inhibit the binding of [$^3$H]-flumazenil to the benzodiazepine binding site of human GABA$_A$ receptors containing the α2 or α3 subunit stably expressed in Ltk$^-$ cells.

Reagents

Phosphate buffered saline (PBS).

Assay buffer: 10 mM KH$_2$PO$_4$, 100 mM KCl, pH 7.4 at room temperature.

[$^3$H]-Flumazenil (18 nM for α1β3γ2 cells; 18 nM for α2β3γ2 cells; 10 nM for α3β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration for α1β3γ2: 1.8 nM; for α2β3γ2: 1.8 nM; for α3β3γ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant $K_i$ can be calculated for each test compound.

The compounds of the accompanying Examples were tested in the above assay, and all were found to possess a $K_i$ value for displacement of [$^3$H]-flumazenil from the α2 and/or α3 subunit of the human GABA$_A$ receptor of 100 nM or less.

EXAMPLE 1

6-(2-Methyl-2H-1,2,4-triazol-3-ylmethoxy)-3-(pyridin-3-yl)-7-(pyrrolidin-1-yl)-1,2,4-triazolo[4,3-b]pyridazine a) 4-Bromo-1,2-dihydropyridazine-3,6-dione A mixture of bromomaleic anhydride (50 g, 283 mmol) and sodium acetate (76.5 g, 562 mmol) in 40% acetic acid/water (750 ml) was treated with hydrazine monohydrate (16.5 ml, 339 mmol) at room temperature under nitrogen. The brown solution was stirred and heated at 100° C. for 18 h. Upon cooling the mixture was poured into water (1 l) and extracted with ethyl acetate (6×500 ml). The combined extracts were dried (MgSO$_4$), filtered and evaporated to afford the title pyridazile (20 g, 37%) as an orange solid. $^1$H NMR (250 MHz, d$_6$-DMSO) 7.68 (br s). MS (ES$^{30}$) 193 [MH]$^+$, 191 [MH]$^+$. This material was used without further purification.

b) 4-Bromo-3,6-dichloropyridazine

A solution of 4-bromo-1,2-dihydropyridazine-3,6-dione (10 g, 52 mmol) in phosphorus oxychloride (100 ml) was stirred and heated at 100° C. under nitrogen for 16 h. Upon cooling the excess phosphorus oxychloride was removed in vacuo. The residue was azeotroped with toluene (×2), then taken up in dichloromethane/water. The mixture was carefully basified with sodium hydrogen carbonate (solid). It was necessary to dilute the mixture further to get two clear layers. The two layers were separated and the aqueous was extracted with dichloromethane (×3). The combined extracts were dried (Na$_2$SO$_4$), filtered and evaporated. The residue was purified by chromatography on silica gel, eluting with dichloromethane to afford the title pyridazine (5.0 g, 42%) as a colourless solid. $^1$H NMR (250 MHz, CDCl$_3$) 7.68 (br s). MS (ES$^{30}$) 230 [MH]$^+$, 228 [MH]$^+$.

c) 3,6-Dichloro-4-(pyrrolidin-1-yl)pyridazine

Pyrrolidine (3.36 ml, 40 mmol) was added to a stirred solution/suspension of 4-bromo-3,6-dichloropyridazine (8.3 g, 36 mmol) and potassium carbonate (13.8 g, 0.1 mol) in dry DMF (100 ml) at room temperature under nitrogen. The mixture was stirred at room temperature for 16 h, then at 60° C. for 3 h. The reaction was poured into water (250 ml). The aqueous was extracted with ethyl acetate (×3). The combined extracts were dried (MgSO$_4$), filtered and evaporated. The residue was purified by chromatography on silica gel, eluting with 0.5% methanol/dichloromethane to afford the title pyridazine (7.2 g, 92%) as a colourless oil. $^1$H NMR (250 MHz, CDCl$_3$) 2.00–2.05 (4H, m), 3.61–3.69 (4H, m), 6.46 (1H, s). MS (ES$^+$) 218 [MH]$^+$, 220 [MH]$^+$.

d) 3-Chloro-6-hydrazino-4-(pyrrolidin-1-yl)pyridazine 3,6-Dichloro-4-(pyrrolidin-1-yl)pyridazine (7.2 g, 33 mmol) and hydrazine hydrate (9.96 g, 0.2 mol) were heated at reflux in dioxan (130 ml) for 6 h. Upon cooling the desired isomer crystallized from the reaction and was collected by filtration (4.1 g, 58%). $^1$H NMR (250 MHz, d$_6$-DMSO) 1.79–1.84 (4H, m), 3.25–3.40 (4H, m), 4.12 (2H, br), 6.09 (1H, s), 7.47 (1H, s). MS (ES$^+$) 214 [MH]$^+$, 216 [MH]$^+$.

e) N-[6- Chloro-5-(pyrrolidin-1-yl)pyridazin-3-yl]-N'-(3-pyridylidene)hydrazine

3-Chloro-6-hydrazino-4-(pyrrolidin-1-yl)pyridazine (1.0 g, 4.69 mmol) and 3-pyridinecarboxaldehyde (443 ml, 4.69 mmol) were stirred in 0.2M hydrochloric acid (20 ml) for 2 h. The precipitated imine was then collected by filtration and dried (1.06 g, 75%). MS (ES$^+$) 303 [MH]$^+$, 305 [MH]$^+$.

f) 6-Chloro-3-(pyridin-3-yl)-7-(pyrrolidin-1-yl)-1,2,4-triazolo[4,3-b]pyridazine Ferric chloride (4.74 g, 17.55 mmol) in ethanol (10 ml) was added dropwise to a solution of imine (1.06 g, 3.51 mmol) in ethanol (60 ml) heated at 60° C. After 6 h the reaction mixture was partitioned between dichloromethane (250 ml) and brine (250 ml). The organic phase was dried (MgSO$_4$), filtered and evaporated. The residue was purified by chromatography on silica gel, eluting with ethyl acetate-hexane mixtures to afford the title pyridazine (0.72 g, 67%). MS (ES$^+$) 301 [MH]$^+$, 303 [MH]$^+$.

g) 6-(2-Methyl-2H-1,2,4-triazol-3-ylmethoxy)-3-(pyridin-3-yl)-7-pyrrolidin-1-yl)-1,2,4-triazolo[4,3-b]pyridazine Sodium hydride (60% dispersion in oil, 16 mg, 0.41 mmol) was added to a solution of (2-methyl-2H-1,2,4-triazol-3-yl)methanol (EP-A-421210; 40 mg, 0.35 mmol) in dry DMF (2 ml) at room temperature. After 1 h at room temperature a solution of 6-chloro-3-(pyridin-3-yl)-7-(pyrrolidin-1-yl)-1,2,4-triazolo[4,3-b]pyridazine (100 mg, 0.33 mmol) was added and the reaction stirred for 18 h. The residue was partitioned between dichloromethane and water. The aqueous was further extracted with dichloromethane (2×100 ml). The combined extracts were dried (Na$_2$SO$_4$), filtered and evaporated. The residue was purified by chromatography on silica gel, eluting with 0–10% ethyl acetate-methanol to afford the title pyridazine (75 mg, 60%). $^1$H NMR (250 MHz, CDCl$_3$) 1.99–2.04 (4H, m), 3.52–3.57 (4H, m), 4.01 (3H, s), 5.65 (2H, s), 6.69 (1H, s), 7.57 (1H, q, J=7.7, 4.8 Hz), 7.97 (1H, s), 8.60–8.68 (2H, m), 9.51 (1H, d, J=1.6 Hz); MS (ES$^+$) 378 [MH]$^+$.

EXAMPLE 2

7-Cyclobutyl-6-(2-methyl-2H-1,2,4-triazol-3-ylmethoxy)-3-(pyridin-3-yl)-1,2,4-triazolo[4,3-b]pyridazine a) 3,6-Dichloro-4-cyclobutylpyridazine 3,6-Dichloropyridazine (10 g) was suspended in water (200 ml) and H$_2$SO$_4$ (19.7 g), cyclobutane carboxylic acid (32.7 g) was added and the reaction degassed under N$_2$ at 70° C. Silver nitrate (2.28 g) was added followed by dropwise addition of ammonium persulfate (45.9 g) in water (120 ml). After an additional 1 h heating at 70° C., the reaction was poured onto ice, basified to pH 8–9 with aqueous ammonium hydroxide and extracted into ethyl acetate (3×500 ml), dried (MgSO$_4$) and evaporated to dryness. Purified with hexane-ethyl acetate mixtures to obtain pure product (13.4 g). $^1$NMR (360 MHz, CDCl$_3$) δ1.57 (2H, m), 1.82 (4H, m), 2.20 (1H, m), 3.30 (1H, m), 7.38 (1H, s); MS (ES$^+$) m/e 217 [MH]$^+$.

b) 3-Chloro-4-cyclobutyl-6-hydrazinopyridazine 3,6-Dichloro-4-cyclobutylpyridazine (22.5 g, 0.11 mol) and hydrazine hydrate (34 ml, 0.66 mol) were heated at reflux in dioxan (280 ml) for 24 h. Upon cooling the desired isomer crystallized from the reaction and was collected by filtration (13.28 g, 64%). $^1$H NMR (250 MHz, d$_6$-DMSO) 1.68–1.86 (1H, m), 2.00–2.11 (3H, m), 2.29–2.38 (2H, m), 3.52–3.61 (1H, m), 4.35 (2H, br), 6.99 (1H, s), 8.06 (1H, br); MS (ES$^+$) m/e 198 [MH]$^+$, 200 [MH]$^+$.

c) 7-Cyclobutyl-6-(2-methyl-2H-1,2,4-triazol-3-ylmethoxy)-3-(pyridin-3-yl)-1,2,4-triazolo[4,3-b]pyridazine 3-Chloro-4-cyclobutyl-6-hydrazinopyridazine was used in an analogous procedure as outlined in Example 1 Steps e), f) and g) to afford the title pyridazine. $^1$NMR (250 MHz, CDCl$_3$) δ1.87–2.01 (1H, m), 2.10–2.29 (3H, m), 2.36–2.47 (2H, m), 3.65–3.77 (1H, m), 4.01 (3H, s), 5.66 (2H, s), 7.63 (1H, dd, J=7.9, 5.1 Hz), 7.94 (1H, d, J=1.5 Hz), 7.97 (1H, s), 8.67–8.76 (2H, m), 9.59 (1H, s); MS (ES$^+$) m/e 363 [MH]$^+$.

EXAMPLE 3

7-(1-Methylcyclopentyl)-6-(2-methyl-2H-1,2,4-triazol-3-ylmethoxy)-3-(pyridin-3-yl)-1,2,4-triazolo[4,3-b]pyridazine Prepared in an analogous procedure as outlined in Example 2 Steps a) and b), using 1-methylcyclopentane carboxylic acid in Step a), and Example 1 Steps e), f) and g), to afford the title pyridazine. $^1$NMR (250 MHz, CDCl$_3$) δ1.31 (3H, s), 1.68–1.95 (8H, m), 3.96 (3H, s), 5.64 (2H, s), 7.40 (1H, dd, J=7.9, 4.8 Hz), 7.60–7.75 (2H, m), 7.94 (1H, s), 7.97–8.02 (2H, m), 8.44–8.47 (1H, m), 8.60–8.69 (2H, m), 8.96 (1H, m); MS (ES$^+$) m/e 439 [MH]$^+$.

EXAMPLE 4

7-Cyclobutyl-6-(2-methyl-2H-1,2,4-triazol-3-ylmethoxy)-3-[3-(pyridin-3-yl)phenyl]-1,2,4-triazolo[4,3-b]pyridazine a) 3-(Pyridin-3-yl)benzaldehyde 3-Bromobenzaldehyde (5 g, 27 mmol), diethyl (pyridin-3-yl)borane (3.97 g, 27 mmol) and potassium carbonate (11 g, 81 mmol) were dissolved in ethylene glycol dimethyl ether and water (40 ml, 2:1) and degassed under N$_2$ then heated at 80° C. for 18 h after addition of tetrakis (triphenylphosphine)palladium(0) (0.2 g). The reaction was then diluted with ethyl acetate and water (200 ml, 1:1) and passed through a hyflo filter plug, the separated organic phase was washed with brine, dried (MgSO$_4$) and evaporated to dryness. Purified on SiO$_2$ eluting with 25–50% ethyl acetate-hexane to afford the title compound (3.6 g, 73%). MS (ES$^+$) m/e 184 [MH]$^+$.

b) 7-Cyclobutyl-6-(2-methyl-2H-1,2,4-triazol-3-ylmethoxy)-3-[3-(pyridin-3-yl)phenyl]-1,2,4-triazolo[4,3-b]pyridazine Prepared in an analogous procedure as outlined in Example 2 using 3-(pyridin-3-yl)benzaldehyde in place of 3-pyridinecarboxaldehyde to afford the title pyridazine. $^1$NMR (250 MHz, CDCl$_3$) δ1.72–1.88 (1H, m), 2.06–2.25 (3H, m), 2.31–2.44 (2H, m), 3.54–3.68 (1H, m), 3.99 (3H, s), 5.61 (2H, s), 7.39 (1H, dd, J=7.7, 4.6 Hz), 7.63–7.71 (2H, m), 7.85 (1H, d, J=1.5 Hz), 7.92 (1H, s), 7.97–8.02 (1H, m), 8.36–8.47 (1H, m), 8.61–8.65 (1H, m), 8.66–8.69 (1H, m), 8.94 (1H, d, J=2 Hz); MS (ES$^+$) m/e 439 [MH]$^+$.

EXAMPLE 5

6-(2-Methyl-2H-1,2,4-triazol-3-ylmethoxy)-3-[3-(pyridin-3-yl)phenyl]-7-(pyrrolidin-1-yl)-1,2,4-triazolo[4,3-b]pyridazine Prepared in an analogous procedure as outlined in Example 1 using 3-(pyridin-3-yl)benzaldehyde in place of 3-pyridinecarboxaldehyde in Step e) to afford the title pyridazine. $^1$NMR (250 MHz, d$_6$-DMSO) δ2.07–2.18 (4H, m), 3.68–3.77 (4H, m), 4.15 (3H, s), 5.94 (2H, s), 7.08 (1H, s), 7.74 (1H, dd, J=8, 4.8 Hz), 7.93 (1H, t, J=7.8 Hz), 8.07–8.10 (1H, m), 8.22 (1H, s), 8.40–8.43 (1H, m), 8.55–8.60 (1H, m), 8.84–8.87 (1H, m), 8.93 (1H, s), 9.23 (1H, d, J=2.2 Hz); MS (ES$^+$) m/e 454 [MH]$^+$.

EXAMPLE 6

7-(1-Methylcyclopentyl)-6-(2-methyl-2H-1,2,4-triazol-3-ylmethoxy)-3-[3-(pyridin-3-yl)phenyl]-1,2,4-triazolo[4,3-b]pyridazine Prepared in an analogous procedure as outlined in Example 3 using 3-(pyridin-3-yl)benzaldehyde in place of 3-pyridinecarboxaldehyde to afford the title pyridazine. $^1$NMR (250 MHz, CDCl$_3$) δ1.31 (3H, s), 1.68–1.92 (8H, m), 3.96 (3H, s), 5.63 (2H, s), 7.38–7.42 (1H, m), 7.64–7.75 (2H, m), 7.94–8.02 (3H, m), 8.47–8.57 (1H, m), 8.58–8.64 (1H, m), 8.72 (1H, s), 8.96 (1H, d); MS (ES$^+$) m/e 467 [MH]$^+$.

EXAMPLE 7

7-Cyclobutyl-6-(3-methylpyridin-2-ylmethoxy)-3-(pyridin-3-yl)-1,2,4-triazolo[4,3-b]pyridazine Sodium hydride (60% dispersion in oil, 13.4 mg, 0.34 mmol) was added to a solution of (3-methylpyridin-2-yl) methanol (38 mg, 0.31 mmol) in dry DMF (1 ml) at room temperature. After 1 h at room temperature a solution of 6-chloro-7-cyclobutyl-3-(pyridin-3-yl)-1,2,4-triazolo[4,3-b] pyridazine (80 mg, 0.28 mmol) was added and the reaction stirred for 18 h. The reaction mixture was diluted with water (10 ml) and stirred for 10 minutes after which time the mixture was filtered and the residue washed, first with water, then with diethyl ether. The residue was purified by chromatography on silica gel, eluting with 0–5% dichloromethane-methanol to afford the title pyridazine (15.1 mg, 14%). $^1$NMR (250 MHz, CDCl$_3$) δ1.83–1.89 (1H, m), 1.96–2.23 (3H, m), 2.28–2.40 (2H, m), 2.43 (3H, s), 3.57–3.67 (1H, m), 5.59 (2H, s), 7.23 (1H, m), 7.45–7.50 (1H, m), 7.58–7.61 (1H, d, J=7.6 Hz), 7.85 (1H, d, J=1.5 Hz), 8.49 (1H, m), 8.66 (2H, m), 9.71 (1H, br s). MS (ES⁺) m/e 373 [MH]⁺.

What is claimed is:

1. A compound of formula I, or a pharmaceutically acceptable salt thereof:

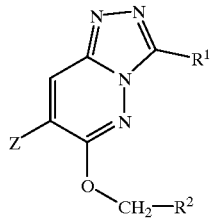

(I)

wherein

Z represents cyclobutyl, 1-methylcyclopentyl or pyrrolidin-1-yl;

$R^1$ represents pyridin-3-yl or pyridin-3-ylphenyl; and $R^2$ represents methyl-triazolyl or methyl-pyridinyl.

2. A compound as claimed in claim 1 wherein $R^2$ represents a ring of structure (a) or (b):

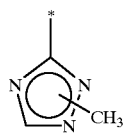

(a)

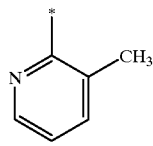

(b)

where the asterisk * denotes the point of attachment of the ring to the remainder of the molecule.

3. A compound as claimed in claim 1 represented by formula IIA, and pharmaceutically acceptable salts thereof:

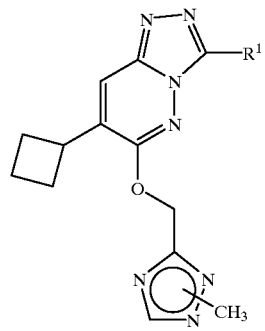

(IIA)

wherein $R^1$ is as defined in claim 1.

4. A compound as claimed in claim 3 represented by formula IIB, and pharmaceutically acceptable salts thereof:

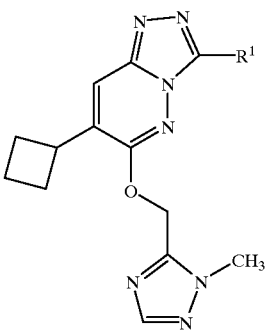

(IIB)

wherein $R^1$ is as defined in claim 1.

5. A compound selected from:
6-(2-methyl-2H-1,2,4-triazol-3-ylmethoxy)-3-(pyridin-3-yl)-7-(pyrrolidin-1-yl)-1,2,4-triazolo[4,3-b]pyridazine;
7-cyclobutyl-6-(2-methyl-2H-1,2,4-triazol-3-ylmethoxy)-3-(pyridin-3-yl)-1,2,4-triazolo[4,3-b]pyridazine;
7-(1-methylcyclopentyl)-6-(2-methyl-2H-1,2,4-triazol-3-ylmethoxy)-3-(pyridin-3-yl)-1,2,4-triazolo[4,3-b]pyridazine;
7-cyclobutyl-6-(2-methyl-2H-1,2,4-triazol-3-ylmethoxy)-3-[3-(pyridin-3-yl)phenyl]-1,2,4-triazolo[4,3-b]pyridazine;
6-(2-methyl-2H-1,2,4-triazol-3-ylmethoxy)-3-[3-(pyridin-3-yl)phenyl]-7-pyrrolidin-1-yl)-1,2,4-triazolo[4,3-b]pyridazine;
7-(1-methylcyclopentyl)-6-(2-methyl-2H-1,2,4-triazol-3-ylmethoxy)-3-[3-pyridin-3-yl)phenyl]-1,2,4-triazolo[4,3-b]pyridazine;
7-cyclobutyl-6-(3-methylpyridin-2-ylmethoxy)-3-(pyridin-3-yl)-1,2,4-triazolo[4,3-b]pyridazine;
and pharmaceutically acceptable salts thereof.

6. A pharmaceutical composition comprising a compound of formula I as defined in claim 1 or a pharmaceutically acceptable salt, thereof in association with a pharmaceutically acceptable carrier.

7. A process for the preparation of a compound as claimed in claim 1, which comprises:

(A) reacting a compound of formula III with a compound of formula IV:

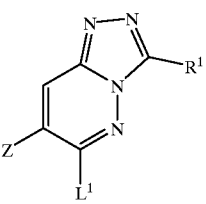

(III)

$R^2$—CH$_2$—OH  (IV)

wherein Z, $R^1$ and $R^2$ are as defined in claim 1, and $L^1$ represents a suitable leaving group.

8. A method for the treatment of anxiety which comprises administering to a patient in need of such treatment an effective amount of a compound of formula I as defined in claim 1 or a pharmaceutically acceptable salt thereof.

9. A method for the treatment and/or prevention of convulsions which comprises administering to a patient in need of such treatment an effective amount of a compound of formula I as defined in claim 1 or a pharmaceutically acceptable salt thereof.

* * * * *